United States Patent [19]

Shoshi

[11] Patent Number: 5,234,623
[45] Date of Patent: Aug. 10, 1993

[54] OPTICALLY ACTIVE OXAZOLINE COMPOUNDS, LIQUID CRYSTAL COMPOSITION CONTAINING THE SAME AND OPTICAL SWITCHING METHOD USING THE SAME

[75] Inventor: Masayuki Shoshi, Yokohama, Japan
[73] Assignee: Ricoh Company, Ltd., Tokyo, Japan
[21] Appl. No.: 914,457
[22] Filed: Jul. 17, 1992

Related U.S. Application Data

[62] Division of Ser. No. 704,935, May 23, 1991, Pat. No. 5,159,084.

[30] Foreign Application Priority Data

May 24, 1990 [JP] Japan .................. 2-132703

[51] Int. Cl.$^5$ .................. C09K 19/34; G02F 1/13
[52] U.S. Cl. .................. 252/299.61; 359/103; 359/62
[58] Field of Search .................. 359/103, 62; 252/299.61; 548/237

[56] References Cited

U.S. PATENT DOCUMENTS

| | | | |
|---|---|---|---|
| 3,726,893 | 4/1973 | Chen et al. | 548/237 |
| 4,052,514 | 10/1977 | Adams et al. | 548/237 |
| 4,514,213 | 4/1985 | Zimmerman | 71/93 |
| 4,880,804 | 11/1989 | Carini et al. | 548/239 |

OTHER PUBLICATIONS

Stamm et al. Chem. Abstr. vol. 104 Entry 53089 (1985).

*Primary Examiner*—Robert L. Stoll
*Assistant Examiner*—C. Harris
*Attorney, Agent, or Firm*—Oblon, Spivak, McClelland, Maier & Neustadt

[57] ABSTRACT

The present invention discloses novel optically active oxazoline compounds represented by the formula (I):

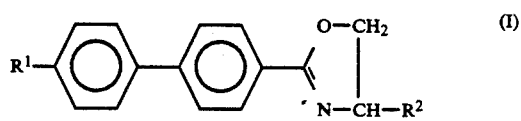

wherein $R^1$ represents an alkoxy group having not more than 20 carbon atoms and $R^2$ represents a low grade alkyl group, as well as liquid crystal compositions containing said compound and a switching mode of high response speed using them. Furthermore, the invention discloses that the devices using said liquid crystal compositions can suitably be used in the opto-electronics field not only for display device but also as various electro-optic devices.

5 Claims, 1 Drawing Sheet

OPTICALLY ACTIVE OXAZOLINE COMPOUNDS, LIQUID CRYSTAL COMPOSITION CONTAINING THE SAME AND OPTICAL SWITCHING METHOD USING THE SAME

This is a division, of application Ser. No. 07/704,935, filed on May 23, 1991, U.S. Pat. No. 5,159,084.

BACKGROUND OF THE INVENTION

The invention relates to novel optically active oxazoline compounds represented by the formula (I):

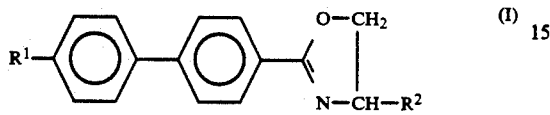

as well as liquid crystal compositions containing them and an optical switching method using them.

So far, conventional liquid crystals have widely been used as materials for display devices. In most cases, these display devices are based on Twisted Nematic (hereinafter, referred to as "TN") mode using nematic liquid crystals, so that they have a disadvantage that almost all the response speeds of them are extremely low, namely, as slow as several milliseconds at the fastest.

In order to eliminate this disadvantage of TN mode, various attempts have been made. For example, a display method using a ferroelectric liquid crystal is disclosed in N. A. Clarks et al., Applied phys. Lett. 36, 899 (1980). This method uses chiral smectic phase, particularly chiral smectic C phase, liquid crystal and attracts attention as a material for a high speed optical switching. Some ferroelectric liquid crystal materials using this principle have already been known [for example, refer to Japanese Patent Application Laid Open No. 70,455 [1989]. However, no material having satisfactory properties has been known yet.

The present inventors have studied intensively in order to develope a liquid crystal having satisfactory properties to be used for an optical switching method. Finally, they have found that the oxazoline compounds represented by the formula (I) satisfies the requirements. The invention has been completed based on this finding.

SUMMARY OF THE INVENTION

Figure 1:
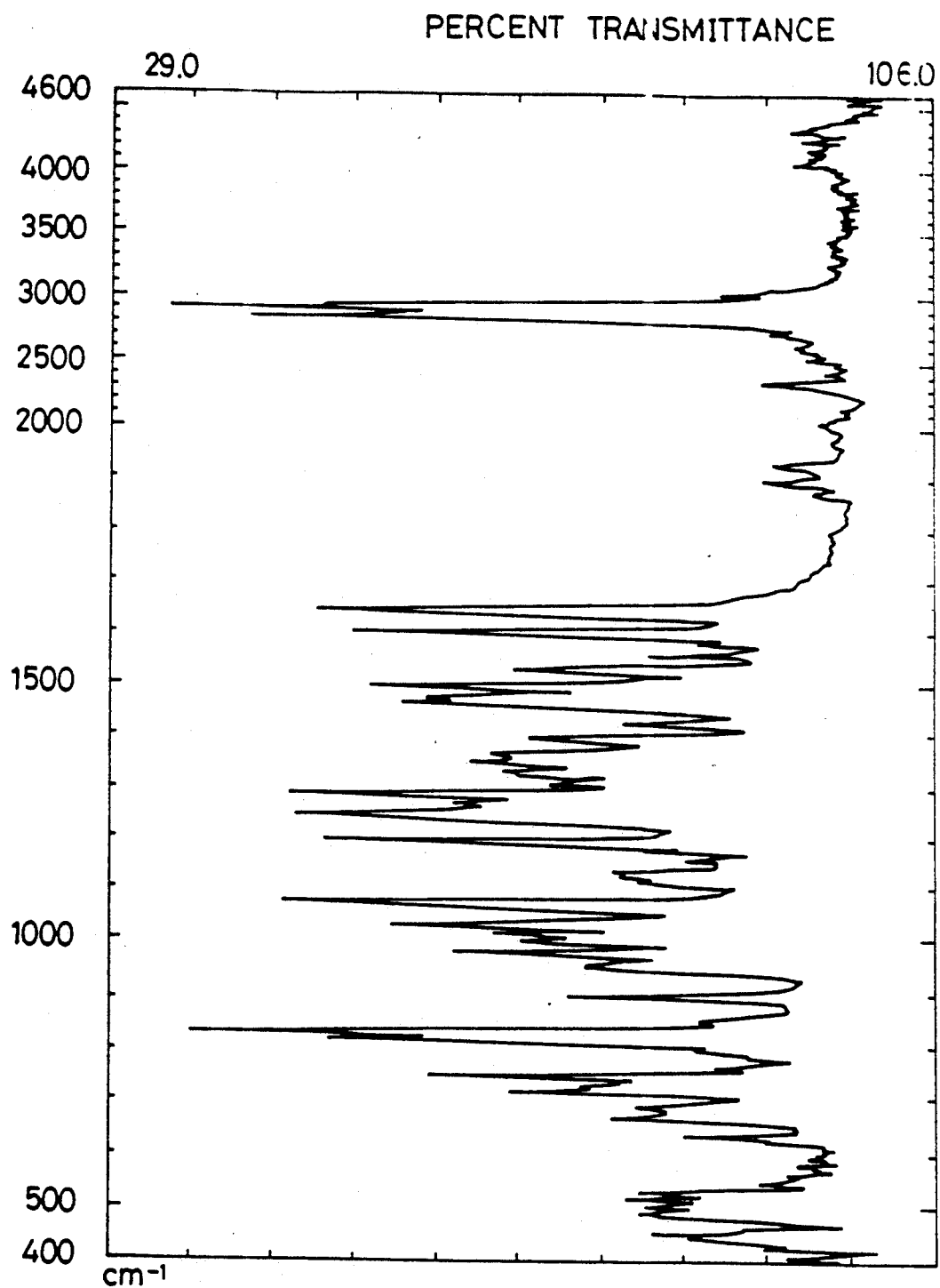
FIG. 1 shows an infrared absorption spectrum of an oxazoline compound prepared in Example 1 of the present invention.

An object of the present invention is to provide novel oxazoline compounds represented by the formula (I):

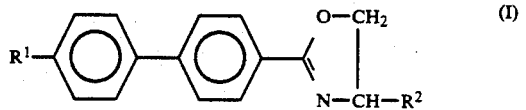

Another object of the present invention is to provide liquid crystal compositions containing a oxazoline compounds represented by the formula (I).

Still another object of the present invention is to provide a liquid crystal material which has high response speed, is chemically stable and suits for an optical switching method.

Yet another object of the present invention is to provide an optical switching method using said optically active oxazoline compounds or a liquid crystal composition thereof.

DETAILED DESCRIPTION OF THE INVENTION

The present invention relates to novel oxazoline compounds represented by the formula (I):

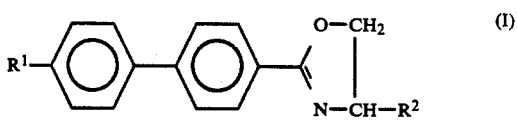

wherein $R^1$ represents an alkoxy group having not more than 20 carbon atoms, $R^2$ is a low grade alkyl group and * indicates a asymmetric carbon atom; as well as a liquid crystal composition containing said compound and an optical switching method using said compound or said composition.

The term, "liquid crystal composition" in the present invention means a composition comprising a liquid crystal and another liquid crystal and/or a compound other than a liquid crystal such as a chiral compound and still having a liquid crystal phase. As a "low grade alkyl group", an alkyl group having 1 to 8 carbon atoms is preferable, the group having 1 to 4 carbon atoms is more preferable, and the group having 1 to 2 carbon atoms is further preferable.

The largest characteristic of the oxazoline compounds represented by the formula (I) of the present invention is that they have an asymmetric carbon atom is their oxazoline ring. Since the compounds have an asymmetric carbon atom at α-position of a group having a dipole moment in a direction perpendicular to a molecular axis, their electric properties, such as spontaneous polarization in a liquid crystal phase are improved remarkably.

Namely, the optically active oxazoline compounds represented by the formula (I) of the present invention show excellent properties as a ferroelectric liquid crystal. They have high response speed and are chemically stable. As for an optical switching method using the oxazoline compound of the present invention, a switching method having a response speed of not more than 1 m second is preferably used. Moreover, by adding said compound to a nematic liquid crystal, the occurrence of reverse domain in a TN type cell can effectively be prevented.

Therefore, the liquid crystal compositions containing the oxazoline compound represented by the formula (I) of the present invention can suitably be used not only for display device, but also as various electro-optic devices such as an electro-optic shutter, an electro-optic iris diaphragm, an optical modulator, a switch for changing optical path for optical communication, a memory and a lens with variable focal length.

Practical examples of the optically active oxazoline compounds represented by formula (I) are shown in Table 1.

TABLE 1

| Compound No. | $R^1$ | $R^2$ |
| --- | --- | --- |
| 1 | $C_{16}H_{33}O-$ | $C_2H_5-$ |
| 2 | $C_{14}H_{29}O-$ | $C_2H_5-$ |
| 3 | $C_{12}H_{25}O-$ | $C_2H_5-$ |
| 4 | $C_{10}H_{21}O-$ | $C_2H_5-$ |
| 5 | $C_9H_{19}O-$ | $C_2H_5-$ |
| 6 | $C_8H_{17}O-$ | $C_2H_5-$ |
| 7 | $C_7H_{15}O-$ | $C_2H_5-$ |
| 8 | $C_6H_{13}O-$ | $C_2H_5-$ |
| 9 | $C_5H_{11}O-$ | $C_2H_5-$ |
| 10 | $C_{16}H_{33}O-$ | $CH_3-$ |
| 11 | $C_{14}H_{29}O-$ | $CH_3-$ |
| 12 | $C_{12}H_{25}O-$ | $CH_3-$ |
| 13 | $C_{10}H_{21}O-$ | $CH_3-$ |
| 14 | $C_9H_{19}O-$ | $CH_3-$ |
| 15 | $C_8H_{17}O-$ | $CH_3-$ |
| 16 | $C_7H_{15}O-$ | $CH_3-$ |
| 17 | $C_6H_{13}O-$ | $CH_3-$ |
| 18 | $C_5H_{11}O-$ | $CH_3-$ |

These compounds of the formula (I) can generally be obtained by reacting a nitrile compound of the formula (II) with an optically active 2-amino-alcohol compound of the formula (III) in the presence of a catalyst.

As a catalyst to be used for the reaction, cadmium acetate, cadmium chloride, zinc chloride and cobalt chloride can be exemplified. The catalyst is added preferably in an amount of $10^{-5}$ to $10^{-1}$ mol per 1 mol of the nitrile compound.

The reaction can usually be carried out without any solvent or in an inert solvent such as an aromatic hydrocarbon. The reaction is carried out at a temperature of 80° to 200° C., preferably 100 to 150° C.

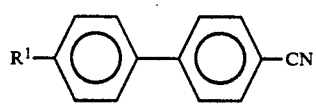
(II)

wherein, $R^1$ represents an alkoxy group having not more than 20 carbon atoms.

(III)

wherein, $R^2$ is a low grade alkyl group, and * indicates an asymmetric carbon atom.

The optically active oxazoline compounds represented by the formula (I) of the present invention show excellent properties as a ferroelectric liquid crystal material. They have high response speed and are chemically stable.

The novel optically active oxazoline compound represented by the formula (I) of the present invention can be used by itself as a ferroelectric liquid crystal material, but, it can also be mixed with a smectic liquid crystal which in itself is not chiral, or with another ferroelectric liquid crystal material, to obtain a liquid crystal composition having an improved performance.

Furthermore, by adding the optically active oxazoline compound represented by the formula (I) to a nematic liquid crystal, the occurrence of reverse domain can effectively be prevented. In this case, said oxazoline compound is used preferably at an amount of 0.01 to 50% by weight of the liquid crystal composition to be obtained.

Moreover, by adding said oxazoline compound to a nematic liquid crystal or to a chiral nematic liquid crystal, it can be used as a chiral nematic liquid crystal composition for a phase transition type liquid crystal device or a guest-host type liquid crystal device. In this case, said oxazoline compound is used preferably at an amount of 0.01 to 80% by weight of the liquid crystal composition to be obtained.

The liquid crystal composition containing the compound of the present invention can suitably be used in the electro-optic devices such as an electro-optic shutter, an electro-optic iris diaphragm, an optical modulator, a switch for changing optical path for optical communication, a memory and a lens with variable focal length.

The compound of the present invention can be used in combination with various liquid crystal compounds, but, it is preferably used in combination with those showing ferroelectric chiral smectic phase, and more preferably in combination with those listed in Table 2.

TABLE 2

| No. | Chemical Structure and Name of Compound | Phase Transition Temperature (°C.) |
|---|---|---|
| 1 | p-dicyloxybenzylidene-p'-amino-2-methylcinnamate<br>$C_{10}H_{21}O-C_6H_4-CH=N-C_6H_4-CH=CH-COOCH_2CH(CH_3)-C_2H_5$ (*) | $Cr \xrightarrow{76°C.} SmC^* \xrightarrow{95°C.} SmA \xrightarrow{117°C.} Iso$; $SmC^* \xrightarrow{63°C.} SmH^*$ |
| 2 | p-hexyloxybenzylidene-p'-amino-2-chloropropylcinnamate<br>$C_6H_{13}O-C_6H_4-CH=N-C_6H_4-CH=CH-COOCH_2CH(Cl)-CH_3$ (*) | $Cr \xrightarrow{60°C.} SmH^* \xrightarrow{64°C.} SmC^* \xrightarrow{78°C.} SmA \xrightarrow{\;} Iso$ |
| 3 | p-decyloxybenzylidene-p'-amino-2-methylbutyl-α-cyanocinnamate<br>$C_{10}H_{21}O-C_6H_4-CH=N-C_6H_4-CH=C(CN)-COOCH_2CH(CH_3)-C_2H_5$ (*) | $Cr \xrightarrow{95°C.} SmA \xrightarrow{104°C.} Iso$; $SmA \xrightarrow{63°C.} SmH^*$; $SmH^* \xrightarrow{70°C.}$ |
| 4 | p-dodecyloxybenzylidene-p'-amino-2-methylbutyl-α-cyanocinnamate<br>$C_{12}H_{25}O-C_6H_4-CH=N-C_6H_4-CH=C(CN)-COOCH_2CH(CH_3)-C_2H_5$ (*) | $Cr \xrightarrow{78°C.} SmA \xrightarrow{104°C.} Iso$; $SmA \xrightarrow{70°C.} SmC^*$; $SmC^* \xrightarrow{47°C.}$ |
| 5 | p-octyloxybenzylidene-p'-amino-2-methylbutyl-α-chlorocinnamate<br>$C_8H_{17}O-C_6H_4-CH=N-C_6H_4-CH=C(Cl)-COOCH_2CH(CH_3)-C_2H_5$ (*) | $Cr \xrightarrow{41°C.} SmA \xrightarrow{66°C.} Iso$; $SmA \xrightarrow{38°C.} SmC^*$; $SmC^* \xrightarrow{27°C.}$ |
| 6 | p-octyloxybenzylidene-p'-amino-2-methylbutyl-α-methylcinnamate<br>$C_8H_{17}O-C_6H_4-CH=N-C_6H_4-CH=C(CH_3)-COOCH_2CH(CH_3)-C_2H_5$ (*) | $Cr \xrightarrow{49°C.} SmC^* \xrightarrow{58°C.} SmA \xrightarrow{94°C.} Iso$ |

TABLE 2-continued

| No. | Chemical Structure and Name of Compound | Phase Transition Temperature (°C.) |
|---|---|---|
| 7 | C$_8$H$_{17}$O—⟨phenyl⟩—CH=N—⟨phenyl⟩—COOCH$_2$CH*(CH$_3$)—C$_2$H$_5$<br>(p-octyloxybenzylidene-p'-amino-2-methylbutylbenzoate) | Cr $\xrightarrow{41°C.}$ SmA $\xrightarrow{66°C.}$ Iso; SmA $\xrightarrow{39°C.}$ SmC* |
| 8 | CH$_3$—C*H(C$_2$H$_5$)—CH$_2$OCO—CH=CH—⟨phenyl⟩—N=N(→O)—⟨phenyl⟩—CH=CH—COOCH$_2$CH*(CH$_3$)—C$_2$H$_5$<br>[4,4'-azoxycinnamic acid-bis(2-methylbutyl)ester] | Cr $\xrightarrow{121°C.}$ SmC* $\xrightarrow{134°C.}$ SmA $\xrightarrow{168°C.}$ Iso |
| 9 | C$_2$H$_5$—C*H(CH$_3$)—CH$_2$O—⟨phenyl(C$_8$H$_{17}$)(OH)⟩—CH=N—⟨phenyl⟩<br>[4-O—(2-methyl)-butylresorcilidene-4'-oxtylaniline] | Cr $\xrightarrow{280°C.}$ SmC* $\xrightarrow{55°C.}$ SmA $\xrightarrow{62°C.}$ Iso |
| 10 | C$_8$H$_{17}$O—⟨phenyl⟩—⟨phenyl⟩—COOCH$_2$CH*(CH$_3$)—C$_2$H$_5$<br>[(2'-methylbutyl)-4'-octyloxybiphenyl-4-carboxylate] | Cr $\xrightarrow{48.5°C.}$ SmA $\xrightarrow{66.5°C.}$ Iso; SmA $\xrightarrow{44°C.}$ SmC* |
| 11 | C$_8$H$_{17}$O—⟨phenyl⟩—COO—⟨phenyl⟩—⟨phenyl⟩—CH$_2$CH*(CH$_3$)—C$_2$H$_5$<br>[4-(2'-methylbutyl)phenyl-4'-octyloxybiphenyl-4-carboxylate] | Cr $\xrightarrow{78°C.}$ Sm3 $\xrightarrow{80°C.}$ SmC* $\xrightarrow{128.3°C.}$ SmA $\xrightarrow{171.0°C.}$ Cho; Cho $\xrightarrow{174.2°C.}$ Iso |
| 12 | CH$_3$—C*H(CHCH$_2$O)—C$_2$H$_5$—⟨phenyl⟩—⟨phenyl⟩—COO—⟨phenyl⟩—OC$_6$H$_{13}$<br>[4-hexyloxyphenyl-4-(2'-methylbutyloxy)biphenyl-4'-carboxylate] | Cr $\xrightarrow{68.8°C.}$ SmC* $\xrightarrow{80.2°C.}$ Cho $\xrightarrow{163.5°C.}$ Iso |

TABLE 2-continued

| No. | Chemical Structure and Name of Compound | Phase Transition Temperature (°C.) |
|---|---|---|
| 13 | CH$_3$<br>C$_2$H$_5$—*CHCH$_2$O—⟨O⟩—⟨O⟩—COO—⟨O⟩—OC$_8$H$_{17}$<br>[4-octyloxyphenyl-4-(2''-methylbutyloxy)biphenyl-4'-carboxylate] | Cr $\xrightleftharpoons[]{76° C.}$ SmC* $\xrightleftharpoons[]{86.6° C.}$ Cho $\xrightleftharpoons[]{155.4° C.}$ Iso |
| 14 | CH$_3$<br>C$_2$H$_5$—*CH(CH$_2$)$_3$—⟨O⟩—⟨O⟩—COO—⟨O⟩—C$_7$H$_{15}$<br>[4-heptylphenyl-4-(4''-methylhexyl)biphenyl-4'-carboxylate] | Cr $\xrightleftharpoons[]{91.5° C.}$ SmC* $\xrightleftharpoons[]{93° C.}$ SmA $\xrightleftharpoons[]{112° C.}$ Cho $\xrightleftharpoons[]{131° C.}$ Iso |
| 15 | CH$_3$<br>C$_2$H$_5$—*CH(CH$_2$)$_3$—⟨O⟩—CH$_2$—⟨O⟩—COO—⟨O⟩—⟨O⟩—CH$_2$*CH—C$_2$H$_5$<br>                                                                      CH$_3$<br>[4-(2''-methylbutyl)phenyl-4-(4''-methylhexyl)biphenyl-4'-carboxylate] | Cr $\xrightleftharpoons[74.3° C.]{68.8° C.}$ Cho $\xrightleftharpoons[81.0° C.]{163.5° C.}$ Iso<br>SmC* $\xrightleftharpoons[]{80.2° C.}$ SmA |

Foot Note:
SmC*; Ferroelectric smectic C phase Iso; Isotropic phase
SmA; Smectic A phase Cr; Crystalline phase
SmH*; Ferroelectric smectic H phase Cho; Choleteric phase
Sm3; Smectic phase

EXAMPLES

TABLE 3

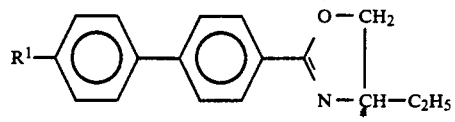

| Ex. | Compound No. | $R^1$ | Elementary Analysis Measured Value (%) | Calculated Value (%) | Phase Transition Temperature (°C.) |
|---|---|---|---|---|---|
| 1 | (3) | n-$C_{12}H_{25}O$— | C 79.98<br>H 9.51<br>N 3.20 | C 79.95<br>H 9.49<br>N 3.22 | Cryst ⇌(105.4° C./93.6° C.) Sc* ⇌(104.3° C.) Iso |
| 2 | (4) | n-$C_{10}H_{21}O$— | C 79.44<br>H 9.25<br>N 3.45 | C 79.56<br>H 9.15<br>N 3.44 | Cryst ⇌(102.0° C./89.5° C.) Sc* ⇌(107.4° C./106.3° C.) Iso |
| 3 | (5) | n-$C_9H_{19}O$— | C 79.29<br>H 9.01<br>N 3.61 | C 79.35<br>H 8.96<br>N 3.56 | Cryst ⇌(104.6° C./88.2° C.) Sc* ⇌(108.6° C./107.5° C.) Iso |
| 4 | (6) | n-$C_8H_{17}O$— | C 79.12<br>H 8.76<br>N 3.69 | C 78.98<br>H 8.96<br>N 3.90 | Cryst ⇌(101.0° C./82.7° C.) Sc* ⇌(110.4° C./109.8° C.) Iso |
| 5 | (7) | n-$C_7H_{15}O$— | C 78.64<br>H 8.66<br>N 3.45 | C 78.86<br>H 8.55<br>N 3.44 | Cryst ⇌(84.9° C./81.6° C.) Sx ⇌(111.4° C./106.6° C.) Sc* ⇌(113.9° C./113.1° C.) Iso |
| 6 | (8) | n-$C_6H_{13}O$— | C 78.64<br>H 8.27<br>N 3.97 | C 78.60<br>H 8.32<br>N 3.99 | Cryst ⇌(88.9° C./86.9° C.) Sx ⇌(120.0° C./117.3° C.) Iso |

The invention will be explained more in detail with reference to the following examples, but, the invention is not limited thereto. As to phase transition temperatures in the examples, the values thereof vary slightly depending on a measurement method and a purity of the compounds.

EXAMPLE 1

Preparation of optically active 2-[4'-(4''-n-dodecyloxyphenyl)phenyl]-5-ethyl-2-oxyazoline [Compound No. 3 in Table 1]

3.65 g (0.01 mol) of 4-n-dodecyloxy-4'-cyanobiphenyl, 1.14 g (0.015 mol) of (R)-2-amino-1-butanol and 0.27 g of cadmium acetate dihydrate were heated and refluxed for 30 hours in toluene. After cooling to room temperature, an inorganic substance was removed by filtration. A residue obtained by distilling out the toluene was treated with a silica gel column chromatography using 1,2-dichloroethane as a developing solvent. The thus obtained crude objected substance was recrystallized three times in ethanol to obtain 2.32 g of pure objected substance [Compound No. 3].

As an angle of rotation of compound $[\alpha]^D = +24.50$ (in chloroform) was observed. The structure of this compound was confirmed by an infrared absorption spectrum, which is shown in FIG. 1.

EXAMPLES 2 to 6

Compounds 4 to 8 in Table 1 were synthesized by the same method as in EXAMPLE 1 except that $R^1$ in the compound of formula (II) was changed accordingly. The chemical structure (only $R^1$ is indicated), elemental analysis value and the phase transition temperature of each of the compounds are listed in Table 3 together with those of Compound 3 of EXAMPLE 1.

[In the above Table 3, Cryst. means crystalline state, Iso means isotropic liquid, Sc* means chiral smectic C phase and Sx means a smectic phase but can not clearly identified.]

EXAMPLE 7

Preparation of optically active 2-[4'-(4'''-n-decyloxyphenyl)phenyl]-6-methyl-2-oxazoline [Compound No. 13 in Table 1]

3.35 g (0.01 mol) of 4-n-decyloxy-4'-cyanobiphenyl, 1.13 g (0.015 mol) of (S)-2-aminopropanol and 0.27 g of cadmium acetate dihydrate were heated and refluxed in toluene for 30 hours. After cooling to room temperature, an inorganic substance was removed by filtration. A residue obtained by distilling out the toluene was treated with a silica gel column chromatography using 1,2-dichloroethane as a developing solvent to obtain a crude objected substance. The crude substance was recrystallized three times in ethanol to obtain 1.42 g of pure objected substance [Compound No. 13].

The structure of this compound was confirmed by an infrared absorption spectrum.

EXAMPLES 8 to 10

Compounds 14 to 16 in Table 1 were synthesized by the same method as in EXAMPLE 7 except that $R^1$ in the nitrile compound of the formula (II) was changed accordingly. The chemical structure (only $R^1$ is indicated), elemental analysis value and the phase transition temperature of each of the compounds are listed in Table 4 together with those of Compound No. 13 of EXAMPLE 7.

TABLE 4

R¹—⟨Ph⟩—⟨Ph⟩—C(=N—*CH—CH₃)(O—CH₂) [cyclic oxazoline]

| Ex. | Compound No. | R¹ | Elementary Analysis Measured Value (%) | Elementary Analysis Calculated Value (%) | Phase transition Temperature (°C.) |
|---|---|---|---|---|---|
| 7 | (13) | n-$C_{10}H_{21}O-$ | C 79.22<br>H 9.04<br>N 3.53 | C 79.35<br>H 8.96<br>N 3.56 | Cryst $\underset{105.3°C.}{\overset{109.6°C.}{\rightleftarrows}}$ Sc* $\underset{107.4°C.}{\overset{113.9°C.}{\rightleftarrows}}$ Iso |
| 8 | (14) | n-$C_9H_{19}O-$ | C 78.98<br>H 8.94<br>N 3.65 | C 79.12<br>H 8.76<br>N 3.69 | Cryst $\underset{106.2°C.}{\overset{116.2°C.}{\rightleftarrows}}$ Sc* $\underset{110.5°C.}{\overset{117.8°C.}{\rightleftarrows}}$ Iso |
| 9 | (15) | n-$C_8H_{17}O-$ | C 78.84<br>H 8.80<br>N 3.84 | C 78.87<br>H 8.55<br>N 3.83 | Cryst $\underset{85.3°C.}{\overset{89.9°C.}{\rightleftarrows}}$ Sc* $\underset{110.5°C.}{\overset{117.5°C.}{\rightleftarrows}}$ Iso |
| 10 | (16) | n-$C_7H_{15}O-$ | C 78.40<br>H 8.50<br>N 3.92 | C 78.60<br>H 8.32<br>N 3.99 | Cryst $\underset{107.7°C.}{\overset{106.3°C.}{\rightleftarrows}}$ Sc* $\underset{113.4°C.}{\overset{122.4°C.}{\rightleftarrows}}$ Iso |

[In the above Table 4, Cryst. means crystalline state, Iso. means isotropic liquid and Sc* means chiral smectic C phase.]

APPLICATION EXAMPLES

APPLICATION EXAMPLE 1

Two transparent electrodes were coated on their surface with polyvinyl alcohol (PVA). The surfaces was then subjected to a parallel orientation treatments by means of rubbing. The electrodes were set facing each other with a distance of 3 μm formed a cell making the PVA films inner sides and the optically active oxazoline compound of EXAMPLE 4 [compound No. 6] was injected into the cell. The cell obtained was placed between two polarizers which were placed perpendicular to each other and obtained a liquid crystal display device. When a voltage of 30 V was applied between the electrodes, a switching action of a high response speed (ca. 100μ second) was observed.

The spontaneous polarization of this liquid crystal was 28.5 nc/cm² at 100° C.

APPLICATION EXAMPLE 2

A composition of the compound No. 3 prepared in Example 1 was prepared by mixing 21% by weight of p-octyloxy-benzoic acid-p'-n-hexyloxyphenylester. This composition had the following phase transition points:

Cryst. $\underset{31.5°C.}{\overset{36.2°C.}{\rightleftarrows}}$ SmC* $\underset{68.0°C.}{\overset{69.1°C.}{\rightleftarrows}}$ SA $\underset{75.4°C.}{\overset{75.8°C.}{\rightleftarrows}}$ Ch $\underset{80.4°C.}{\overset{81.2°C.}{\rightleftarrows}}$ Iso Wherein
 Cryst: Crystalline state,
 SmC*: Ferroelectric smectic C phase,
 Ch: Cholesteric phase
 Iso: Isotropic liquid.

What is claimed is:

1. A display device and an electro-optic device provided with a liquid crystal composition with an optical switch comprising an optically active oxazoline compound represented by the formula (I):

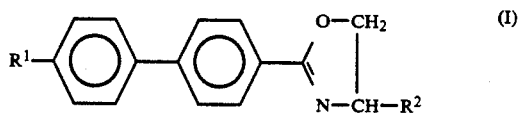

(I)

wherein R¹ is an alkoxy group having not more than 20 carbon atoms and R² is an alkyl group having 1 to 8 carbon atoms.

2. A display device and an electro-optic device provided with an optical switch comprising an optically active oxazoline compound of the formula (I) as a liquid crystal:

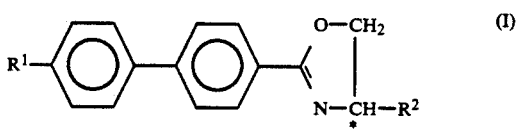

(I)

wherein R¹ and R² have the same meaning as those in claim 1.

3. The display device and the electro-optic device according to claim 1, wherein said composition further contains a nematic liquid crystal.

4. The display device and the electro-optic device according to claim 1, wherein said composition further contains a chiral nematic liquid crystal.

5. The electro-optic device according to claims 2 or 3, wherein said device is selected from the group consisting of an electro-optic shutter, an electro-optic iris diaphragm, an optical modulator, a switch for changing optical path for optical communication, a memory and a lens having variable focal length.

* * * * *